United States Patent

Krenkel

[11] Patent Number: 5,087,259
[45] Date of Patent: Feb. 11, 1992

[54] ORTHOPEDIC PLATE TO FIX IN POSITION PORTIONS OF BONE WHEN RECONSTRUCTING THE LOWER JAW

[76] Inventor: Christian Krenkel, Moosstrasse 126, A.5020 Salzburg, Austria

[21] Appl. No.: 626,297

[22] Filed: Dec. 12, 1990

[30] Foreign Application Priority Data

Dec. 22, 1989 [AT] Austria .................. 2922/89

[51] Int. Cl.⁵ .................................. A61F 5/00
[52] U.S. Cl. ............................ 606/60; 623/16
[58] Field of Search ............ 128/68, 69, 76 R; 623/16, 18; 606/53, 60, 86, 87, 72; 433/20, 176, 180, 181, 215

[56] References Cited

U.S. PATENT DOCUMENTS

| | | | |
|---|---|---|---|
| 4,308,861 | 1/1982 | Kelly | 128/68 |
| 4,448,191 | 5/1984 | Rodnyansky et al. | 628/69 |
| 4,726,808 | 2/1988 | Collins | 623/16 |
| 4,818,226 | 4/1989 | Berendt et al. | 433/20 |
| 4,897,036 | 1/1990 | Kesling | 433/20 |

FOREIGN PATENT DOCUMENTS

| | | | |
|---|---|---|---|
| 290138 | 11/1988 | European Pat. Off. | 128/68 |
| 3538842 | 5/1987 | Fed. Rep. of Germany | 606/72 |
| 1181651 | 9/1985 | U.S.S.R. | 623/18 |
| 1428355 | 10/1988 | U.S.S.R. | 128/68 |

*Primary Examiner*—Richard J. Apley
*Assistant Examiner*—Linda C. M. Dvorak
*Attorney, Agent, or Firm*—Wenderoth, Lind & Ponack

[57] ABSTRACT

Described is a splint to fix in position portions of bone (5',5") when reconstructing the lower jaw, where the two end regions (1) of the splint made especially of titanium exhibit openings (6) to receive attachment screws (3), the center portion (2) of the splint can be permanently deformed by bending, and the cross section of the center portion (2) of the splint is a square (7).

3 Claims, 1 Drawing Sheet

ORTHOPEDIC PLATE TO FIX IN POSITION PORTIONS OF BONE WHEN RECONSTRUCTING THE LOWER JAW

BACKGROUND OF THE INVENTION

1. Field of the Invention

The invention relates to an orthopedic plate or splint (the two terminologies hereinafter considered synonymous) to fix in position portions of bone when reconstructing the lower jaw, where the two end regions of the splint made especially of titanium exhibit openings to receive attachment screws, and the center portion of the splint lying between the end regions in the plane extending normally relative to the axis of these openings can be 2. Description of the Prior Art Following mandibulectomy in which two resection stumps remain, which are suitable to receive at least three osteosynthesis screws, a reconstruction can be made with such splints. As described in Plastische und Wiederherstellungschirurgie des Alters [Plastic and Rehabilitation Surgery of the Elderly], Springer-Verlag Berling Heidelberg, 1986, page 67 "Tumoresektion und gleichzeitige funtionelle Rekonstruktion bei orofazialen Tumoren alter Menschen [Tumor Resection and simultaneous functional Reconstruction of orofacial Tumors of old People]" by H. Matras and Ch. Krenkel, in Der zahnlose Unterkiefer, seine chirurgischprothetische Rehabilitation [The toothless Lower Jaw, its surgical-prosthetic Rehabiltion[, Springer-Verlag, 1988, pages 11 to 124 "Die präprothetischfunktionsgerechte Unterkieferrekonstruktion [The Preprosthetic-functional Reconstruction of the Lower Jaw]" H. Matras and Ch. Krenkel and in Acta Chirurgica Austriaca 1986, issue 3, page 254, in such cases it is desirable to manufacture as soon as possible the bone of the lower jaw, for example by means of iliac crest transplants that are screwed together. These transplants must be protected, on the one hand, from too much stress due to the masticatory musculature, on the other hand, functional stimuli should not be prevented due to the transplant being fixed too rigidly in position.

The splints described in the aforementioned prepublication have withstood the test in principle following resections with benign and malignant tumors, gunshot wounds and congenital deformations. The possibility of bending the splint in a plane extending normally with respect to the axis of the screw holes is obtained, however, through lateral notches into the center portion of the splint whose cross-section is rectangular, thus resulting in a very difficult removal of the splint from the tissue which occurs on average after nine months. This applies especially when the plate is provided with holes over its entire length in order to cut to length as needed.

In order to avoid the above drawbacks, splints can be made available first of all in lengths that occur in practice and that exhibit only screw holes at the end regions so that growth of tissue into the remaining open holes is avoided. However, this does not solve the problem of making the center portion of the splint also bendable in a plane extending parallel to the axis of the openings. To achieve this, it is conceivable to equip the center rib with a circular cross-section. However, this makes it difficult to judge in the course of the operation how the spatial curve described by the rib is curved. Since, on the other hand, a rib with a continuously constant rectangular cross section in the plane extending parallel to the longer side of the rectangle is hardly bendable, it is provided according to the invention that the cross section of the center portion of the splint is a square.

SUMMARY OF THE INVENTION

Such a splint with a center portion exhibiting a square cross section can be bent easily with pliers in the plane extending parallel to the sides of the square, a feature that enables simple control of the targeted spatial configuration. In particular it is also possible to turn the center portion around its own axis, wherein one and the same plate bender can be used regardless of which surface of the splint points towards the surgeon.

To avoid injuries, the corners of the square forming the cross section will be rounded off in an advantageous manner, but this rounding off may not go so far that when turning the splint around its longitudinal axis, the plate bender slips.

Other details of the invention are explained with reference to the drawings as follows.

DESCRIPTION OF THE PREFERRED EMBODIMENTS

Figure 1:
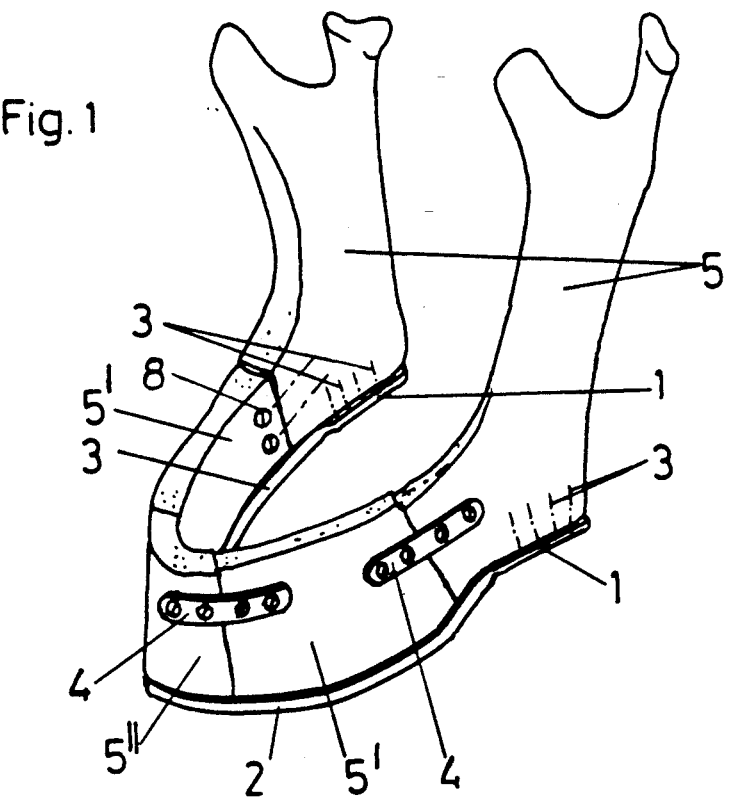
FIG. 1 is a graphic view of a lower jaw reconstructed using the splint of the invention.
Figure 2:
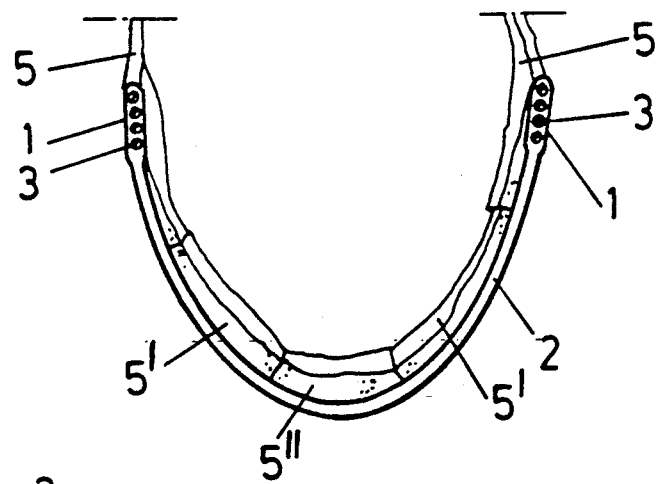
FIG. 2 is a related bottom view.
Figure 3:
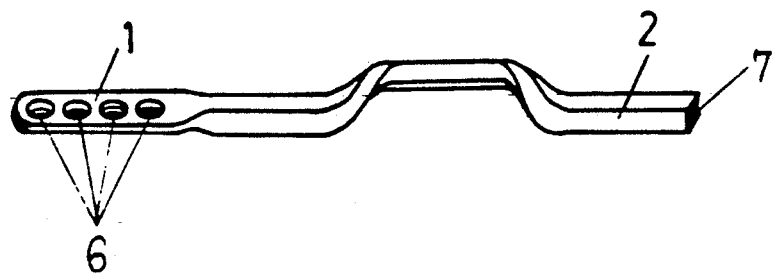
FIG. 3 is a view of a splint of the invention.

FIG. 1 represents a lower jaw, which is resected as far as parts 5 and has been reconstructed by means of transplants and 5', for example from the iliac crest of the patient. The portions of the bone are connected, on the one hand, with traction screws 8 or osteosynthesis plates 4, on the other hand with splints that are designed according to the invention and shown in FIG. 3. The splint exhibits flat end regions 1, which are provided with openings 6 to receive screws 3. Important for the invention is that the cross section 7 of center portion 2 of the splint is square. The corners of this square can be slightly rounded off, the corners of the center portion are thus dulled. However, the deviations from the strictly square shape are to remain in any event so small that a plate bender can be applied to center portion 2 in order to twist said center portion, for example, out of its axis. This option must exist because the splint according to the invention does not always have to extend at the bottom of the lower jaw, as shown in FIG. 1, but rather can be directed on the outside or alternatingly on the outside and bottom.

I claim:

1. An orthopedic plate to fix in position portions of bone during reconstruction of the lower jaw, comprising an elongate body having opposite flat end regions and a center portion; said end regions having a width and a thickness, and having a plurality of openings through the thickness for receiving attachment screws; said center portion extending between said end regions in a plane perpendicular to the axis of said openings, wherein said center portion is composed of a material which can be permanently deformed by bending; and wherein the center portion of the plate is essentially in the shape of a square in cross-section.

2. Orthopedic plate as claimed in claim 4, wherein the corners of the square forming the cross-section are rounded off.

3. Orthopedic plate as claimed in claim 1, wherein said opposite end regions are comprised of titanium.

* * * * *